United States Patent [19]

Inomata et al.

[11] Patent Number: 5,169,971
[45] Date of Patent: Dec. 8, 1992

[54] PROCESS FOR PRODUCING NORCAMPHANE DICARBONITRILES

[75] Inventors: Masamitu Inomata; Naokazu Shiotani; Kazuo Koshizuka; Minato Karasawa, all of Chiba, Japan

[73] Assignee: Mitsui Toatsu Chemicals, Inc., Tokyo, Japan

[21] Appl. No.: 879,723

[22] Filed: May 6, 1992

Related U.S. Application Data

[63] Continuation of Ser. No. 613,864, Dec. 4, 1990, abandoned.

[30] Foreign Application Priority Data

Apr. 4, 1989 [JP] Japan ................... 1-83970

[51] Int. Cl.$^5$ ............................................ C07C 253/10
[52] U.S. Cl. ...................................... 558/338; 558/339
[58] Field of Search ............................ 558/338, 339

[56] References Cited

U.S. PATENT DOCUMENTS

| | | | |
|---|---|---|---|
| 2,666,748 | 1/1954 | Arthur, Jr. et al. | 252/438 |
| 2,666,780 | 1/1954 | Arthur, Jr. et al. | 260/465.3 |
| 3,496,217 | 2/1970 | Drinkard, Jr. et al. | 260/465.8 |
| 3,655,723 | 4/1972 | Drinkard, Jr. | 558/338 |
| 3,752,839 | 8/1973 | Drinkard, Jr. et al. | 260/465.8 R |
| 3,766,237 | 10/1973 | Chia et al. | 558/338 |
| 3,850,973 | 11/1974 | Seidel et al. | 558/338 |
| 3,925,445 | 12/1975 | King et al. | 558/338 |
| 4,125,068 | 11/1978 | Linnerz et al. | 100/19 R |
| 4,215,068 | 7/1980 | Wu et al. | 558/338 |
| 4,330,483 | 5/1982 | Rapoport | 558/338 |

OTHER PUBLICATIONS

Brown et al., Am. Chem. Soc. Div. Pet. Chem. Preprints, 14 (pp. B-29 to B34), (1969).
Chatt et al., J. Chem. Soc., London (1960), pp. 1378 to 1388.
Meriwether et al., J.A.C.S., 81, pp. 4200 to 4208, (1959).

Primary Examiner—Joseph Paul Brust
Attorney, Agent, or Firm—Burns, Doane, Swecker & Mathis

[57] ABSTRACT

The present invention relates to the production of a norcamphane dicarbonitrile and is directed to solving the problems of low conversion from the starting material, low selectivity and uneconomical production.

According to the present invention, a norcamphane dicarbonitrile is produced by hydrocyanation of bicyclo [2,2,1]-5-heptene-2-carbonitrile in the presence of a zero-valent nickel complex catalyst and a Lewis acid.

32 Claims, No Drawings

PROCESS FOR PRODUCING NORCAMPHANE DICARBONITRILES

This application is a continuation, of application Ser. No. 07/613,864, filed Dec. 4, 1990, now abandoned.

TECHNICAL FIELD

The present invention relates to a process for producing a norcamphane dicarbonitrile (hereinafter referred to as "NDC") compound, and more particularly, to a process for producing a norcamphane dicarbonitrile compound mainly composed of 2,5-norcamphane dicarbonitrile (hereinafter referred to as "2,5-NDC") and 2,6-norcamphane dicarbonitrile (hereinafter referred to as "2,6-NDC") comprising hydrocyanation of bicyclo [2,2,1]-5-heptene-2-carbonitrile (hereinafter referred to as "BHC").

BACKGROUND ART

In the past only the following processes for producing NDC's by hydrocyanation of BHC were known:
(i) A process where a catalyst system comprising a cobalt carbonyl catalyst and triphenyl phosphine is used (see U.S. Pat. Nos. 2,666,780 and 2,666,748).
(ii) A process where a catalyst system composed of tetrakis (triaryl phosphite) palladium and triphenyl phosphite is used (Am. Chem. Soc. Div. Pet. Chem. Preprints, 14, B 29 (1969), etc.
(iii) U.S. Pat. No. 3,496,217 discloses a process for producing dinitriles such as adiponitrile and the like which comprises hydrocyanation of olefins such as 3-pentenenitrile, 4-pentenenitrile and the like in the presence of a zero-valent nickel complex and a promoter such as zinc chloride and the like.
(iv) U.S. Pat. Nos. 3,655,723 and 3,766,237 disclose examples where a zero-valent nickel complex and zinc chloride are used upon hydrocyanation of methyl bicyclo (2,2,1)-5-heptene-2-carboxylate as a bicyclo (2,2,1)-5-heptene compound, and U.S. Pat. No. 3,752,839 discloses examples using a zero-valent palladium catalyst and zinc chloride catalyst system.
(v) Examples using a zero-valent nickel complex and zinc chloride are disclosed in U.S. Pat. Nos. 3,850,973 and 3,925,445 which are directed to a process for producing cyanoolefins by hydrocyanation of butadiene and bicyclo (2,2,1)-2,5-heptadiene, and in U.S. Pat. No. 4,215,068 which is directed to a process for producing a dicyanocyclopentane by hydrocyanation of cyclopentadiene and then hydrocyanation of the resulting product, cyanocyclopentene.

However, it can not be said that prior art has proposed a satisfactory process for producing NDC's.

For example, in (i) above, the yield of NDC's is only about 62% when a cobalt catalyst and triphenyl phosphine are used in an amount of 15-30% by weight based on BHC and hydrogen cyanide is used in a large amount, that is, 1.4 time that of BHC followed by carrying out the reaction at 130° C. for 8 hours.

According to the production process of (ii) above, since an expensive palladium catalyst is used, recovery of the catalyst is troublesome, and the reaction temperature is so high (150°-190° C.) that handling is difficult, and further, as is clear from the low yield, the catalytic activity is low.

In the hydrocyanation of olefins and dienes in (iii) and (v), a zero-valent nickel complex is used in a large amount, i.e. about 0.5-2.5 mol % based on the olefin while the conversion of olefins and dienes is 30-80% and the yield of the end product, dinitriles, is as low as 30-70%. In addition, products and yields are not disclosed in the hydrocyanation of bicyclo (2,2,1)-5-heptene compounds in (iv) above.

An object of the present invention is to solve the above-mentioned problems of the prior art and produce NDC's at a high conversion, high selectivity and advantageously from an economical point of view.

DISCLOSURE OF INVENTION

The present invention is a process for producing a norcamphane dicarbonitrile (NDC) comprising hydrocyanation of bicyclo [2,2,1]-5-heptene-2-carbonitrile (BHC) in the presence of a zero-valent nickel complex catalyst and a Lewis acid.

BHC used in the present invention may be easily obtained in a high yield by the Diels-Alder reaction of cyclopentadiene with acrylonitrile by heating, and it is preferable to use a product obtained by purifying the reaction product by distillation or the like.

The zero-valent nickel complex catalyst used in the present invention can be represented by the general formula (I), $$Ni[(A)(B)(C)(D)] \qquad (I)$$

where A,B,C and D are, similar or dissimilar, and are neutral ligands represented by the general formula (II), $$P(x)(y)(z) \qquad (II)$$

where P is a phosphorus, x, y and z are, similar or dissimilar, OR where R is selected from the group consisting of alkyl having 18 carbon atoms or less and aryl having 18 carbon atoms or less.

Examples of the neutral ligands include triaryl phosphites such as triphenyl phosphite and the like; tri-substituted phenyl phosphite such as tri-halo substituted phenyl phosphite, tri-alkoxy substituted phenyl phosphite, tri-alkyl substituted phenyl phosphite; and trialkyl phosphites, and mixtures thereof.

Concrete examples of tri-substituted phenyl phosphites include tri-m- or p-tolyl phosphite, tri-m or p-chlorophenyl phosphite, tri-m or p-methoxyphenyl phosphite, and tri-m or p-nonylphenyl phosphite. Concrete examples of trialkyl phosphites include triethyl phosphite, triisopropyl phosphite, and tributyl phosphite.

One or more of the neutral ligands, A, B, C and D can leave the zero-valent nickel complex catalyst under most reaction conditions.

The neutral ligands are preferably triaryl phosphites, in particular, triphenyl phosphite, tri-m or p-tolyl phosphite, and tri-m or p-nonylphenyl phosphite.

Exemplary suitable zero-valent nickel complex catalysts include tetrakis (triphenyl phosphite) nickel; tetrakis (tri-substituted phenyl phosphite) nickels, for example, tetrakis (tri-halo-substituted phenyl phosphite) nickel, tetrakis (tri-alkoxy-substituted phenyl phosphite) nickel and tetrakis (tri-alkyl-substituted phenyl phosphite) nickel; and tetrakis (trialkyl phosphite) nickel.

As concrete examples of tetrakis (tri-substituted phenyl phosphite) nickels are those where the tri-substituted phenyl phosphite is selected from tri-m- or p-tolyl phosphite, tri-m- or p-chlorophenyl phosphite, tri-m- or p-methoxyphenyl phosphite, tri-m- or p-nonylphenyl phosphite and the like.

Further, exemplary suitable zero-valent nickel complex catalysts include tetrakis (trialkyl phosphite)

nickel, for example, tetrakis (triethyl phosphite) nickel, tetrakis (triisopropyl phosphite) nickel, and tetrakis (tributyl phosphite) nickel.

In the present invention, it is preferably to carry out hydrocyanation in the presence of a neutral ligand so as to enhance the activity of the zero-valent nickel complex catalyst and prolong the life of the catalyst.

The amount of the neutral ligand used is usually one mole or more, preferably 2–32 moles, more preferably 4–16 moles based on one mole of the existing zero-valent nickel complex catalyst. An amount exceeding 32 moles does not adversely affect the reaction itself, but is not always economically preferable taking into consideration the post-treatment of the reaction product fluid and the loss of the neutral ligand upon the purification and recovery procedure.

Taking into account the neutral ligand coordinate in the zero-valent nickel complex, the amount of the total neutral ligand used is usually 5 moles or more, preferably 6–36 moles, more preferably 8–20 moles per mole of the zero-valent nickel complex catalyst.

Preparation of the zero-valent nickel complex catalyst is disclosed, for example, in U.S. Pat. No. 3,328,443, J. Chem. Soc. London, 1378–1389 (1960), J. Am. Chem. Soc., 81, 4200–4209 (1959) and Inorg. Synth., 13, 108 or 112.

The amount of the zero-valent nickel complex catalyst used in terms of the molar ratio of zero-valent nickel complex catalyst to BHC is usually from 1:5000 to 1:20, preferably from 1:2000 to 1:100. When the molar ratio exceeds 1:20, there is not obtained an advantage corresponding to the increase in the amount of the catalyst and thereby it is not economical.

In the present invention, a Lewis acid is present as a promoter. As a Lewis acid, there is, for example, a compound comprising a center metal having a vacant orbit.

Examples of Lewis acids are compounds composed of an anion and a metallic cation selected from elements of groups IIa, IIIa, IVa, Va, VIa, VIIa, VIII, Ib, IIb, IIIb, and IVb of the Periodic Table.

Examples of the metallic cation are zinc, cadmium, beryllium, aluminum, gallium, indium, silver, titanium, zirconium, hafnium, germanium, tin, vanadium, niobium, scandium, chromium, molybdenum, tungsten, manganese, rhenium, palladium, thorium, erbium, iron, cobalt, and boron ions.

Examples of anions are halogen anions such as chlorine, bromine, fluorine and iodine, anions of lower fatty acids of $C_2$–$C_7$, $HPO_3^{2-}$, $H_2PO_2^-$, $CF_3CO_2^-$, $OSO_2C_7F_{15}^-$, and $SO_4^{2-}$.

Particularly preferable metallic cations are zinc, cadmium, titanium, tin, vanadium, chromium, aluminum and the like ions and examples of anions are chlorine ion, iodine ion, $HPO_3^{2-}$, $H_2PO_2^-$ and the like.

In addition, examples of a Lewis acid are organic boron, for example, trialkyl boron such as triethyl boron, triphenyl boron and the like, and metal alkoxides such as aluminum isopropoxide and titanium isopropoxide.

Examples of preferable Lewis acids are zinc chloride, cadmium chloride, cadmium iodide, chromium chloride, boron trichloride, and triphenyl boron, and zinc chloride is particularly preferable.

A Lewis acid as a promoter can prolong the life of the catalyst and the amount of Lewis acid used is usually 0.05–50 moles, preferably 0.5–5 moles per mole of the zero-valent nickel complex catalyst.

In the hydrocyanation of the present invention, the neutral ligand can behave as a solvent, but additionally other solvent or solvents may be used.

The solvents used include, for example, aryl compounds containing at least one hydroxyl group and having 6–20 carbon atoms, preferably, 6–10 carbon atoms, and if desired, may be the above-mentioned aryl compounds having at least one substituent selected from the group consisting of fluoro, chloro, bromo, iodo, nitro, cyano, and hydrocarbon groups having 1–9 carbon atoms. The aryl compounds are, for example, phenol, p-cresol, resorcinol, β-naphthol, p-chlorophenol, p-nitrophenol, p-butylphenol and analogs thereof.

As other solvents, there may be mentioned, for example, aromatic hydrocarbons such as benzene, toluene, xylene, ethylbenzene and the like; nitriles such as acetonitrile, benzonitrile and the like; ethers such as dioxane, o-dimethoxybenzene, tetrahydrofuran, dimethoxyethane, diethoxyethane and the like; chloroaromatic hydrocarbons such as o-dichlorobenzene, p-dichlorobenzene and the like; and analogs thereof.

According to the present invention, the hydrocyanation of BHC can be effected, for example, such that prescribed amounts of the above-mentioned zero-valent nickel complex catalyst, Lewis acid, BHC, and neutral ligand (or solvent) are fed to a reactor and then hydrogen cyanide is introduced into the reaction fluid under stirring at a prescribed temperature. Hydrogen cyanide may be introduced thereinto in the form of either gaseous hydrogen cyanide or liquid hydrogen cyanide.

Hydrogen cyanide may be used alone, but, from the standpoint of handling, it is desirable to dilute hydrogen cyanide to an appropriate concentration with a gas inert to the reaction such as nitrogen, helium, argon and the like.

Liquid hydrogen cyanide may be used alone or may be diluted with a solvent such as benzene, xylene and the like to an appropriate concentration for use.

Hydrogen cyanide is used usually in an amount of 0.2–1.5 mole, preferably 0.5–1.2 mole per mole of BHC.

The reaction temperature of hydrocyanation of BHC is usually in the range of from −20° to 200° C., preferably from 20° to 130° C., more preferably from 50° to 100° C.

The reaction pressure is, in usual, preferably atmospheric pressure, and the reaction may be effected at a pressurized system, but there is not any remarkable advantage due to the high pressure.

The hydrocyanation of BHC is usually effected batchwise, but a continuous reaction system may be employed such that BHC, hydrogen cyanide, zero-valent nickel complex catalyst, Lewis acid, neutral ligand and the like are continuously fed to a reactor.

NDC's produced by the present invention can be obtained as a mixture containing 2,5-NDC and 2,6-NDC as the components.

After completion of the reaction, the resulting reaction product fluid containing NDC's produced by hydrocyanation of BHC at a high concentration is subjected to a post-treatment, for example, for recoverying effective components as catalyst and the like, that is, extraction with an organic solvent or extracting Lewis acids and inorganic materials with water, and then NDC's are obtained by distillation.

Distillation of NDC's is preferably carried out at a pressure of 0.3–0.5 mm Hg to collect a distillate fraction at 120°–130° C. as NDC's.

According to the present invention, NDC's can be produced at high conversion and at high selectivity economically by hydrocyanation of BHC in the presence of a zero-valent nickel complex catalyst and a promoter system composed of a Lewis acid, and therefore, the process for producing NDC's is very advantageous.

Best Mode for Carrying Out the Invention

For the purpose of describing the present invention more in detail, the following examples are given. Comparative examples are also given to help the understanding of the present invention.

Analysis of the reaction fluid was conducted by gas chromatography.

EXAMPLE 1

A 50 ml. glass round-bottom flask fitted with a stirrer, a thermometer, a gas inlet tube, a cooler and the like was charged with BHC 27.55 g (229 m mol), tetrakis (triphenyl phosphite) nickel 0.79 g (0.608 m mol), zinc chloride 0.44 g (3.2 m mol) and triphenyl phosphite 3.10 g (10.0 m mol), purged with a nitrogen gas sufficiently, and the contents in the reactor was kept at 95° C. with stirring.

Then, nitrogen gas was introduced into a receiving vessel containing liquid hydrogen cyanide cooled with ice water and bubbled through the liquid hydrogen cyanide to generate a hydrogen cyanide gas and said gas was introduced into the reaction fluid in the reactor.

The flow rate of nitrogen gas was 55-60 ml/min. 7.0 g (259 m mol) of hydrogen cyanide gas in total was fed to the reactor over 5 hours and then the reaction was completed.

The reaction fluid was cooled and analyzed, and it was found that the conversion of BHC was 97.5% and selectivity of NDC's 94.4%.

EXAMPLES 2-6

The procedure of Example 1 was repeated using the same reactor as in Example 1 except that molar ratio of BHC, tetrakis (triphenyl phosphite) nickel, zinc chloride, triphenyl phosphite and hydrogen cyanide, temperature and feeding time of hydrogen cyanide gas were changed.

The results are shown in Table 1.

EXAMPLE 7

The reaction of Example 1 was repeated except that liquid hydrogen cyanide cooled with ice was directly fed to the reactor using a microtube pump in place of the hydrogen cyanide gas.

The flow rate of liquid hydrogen cyanide was 2-2.5 ml/hr, and 7.0 g (259 m mol) of liquid hydrogen cyanide in total was fed to the reactor over 5 hours and the reaction was completed.

The reaction fluid was cooled and analyzed. It was found that the conversion of BHC was 99.9% and selectivity of NDC's 99.8% (see Table 2).

EXAMPLES 8-9

The procedure of Example 7 was repeated except that the molar ratio of liquid hydrogen cyanide, temperature, and feeding time of hydrogen cyanide were changed.

The results are shown in Table 2.

EXAMPLES 10-13

The procedure of Example 6 was repeated with the same feed as in Example 6 except that the zero-valent nickel complex catalyst and the neutral ligand were replaced with the catalyst systems shown in Table 3. The results are shown in Table 3.

EXAMPLES 14-18

The hydrocyanation of Example 6 was repeated with the same feed as in Example 6 except that Lewis acids in Table 4 were used in place of zinc chloride. The results are shown in Table 4.

TABLE 1

|  | Molar ratio | | | | Temperature (°C.) | HCN Feeding Time (hr) | BHC Conversion (%) | NDC's Selectivity (%) |
| --- | --- | --- | --- | --- | --- | --- | --- | --- |
|  | BHC | Ni (O) | ZnCl$_2$ | P (OPh)$_3$ | Gaseous HCN | | | |
| Example 1 | 100 | 0.27 | 1.41 | 4.16 | 113 | 95 | 5 | 97.5 | 94.4 |
| Example 2 | 100 | 0.13 | 0.64 | 1.25 | 130 | 95 | 4.8 | 100.0 | 95.5 |
| Example 3 | 100 | 0.066 | 0.32 | 0.50 | 136 | 95 | 2.8 | 80.7 | 99.0 |
| Example 4 | 100 | 0.13 | 0.65 | 1.00 | 99 | 81 | 4.5 | 91.3 | 97.0 |
| Example 5 | 100 | 1.00 | 1.00 | 1.50 | 120 | 130 | 2.5 | 100.0 | 99.8 |
| Example 6 | 100 | 0.14 | 0.16 | 1.01 | 131 | 50 | 4.5 | 99.9 | 99.4 |

Ni (O): Tetrakis (triphenyl phosphite) nickel
P (OPh)$_3$: Triphenyl phosphite

TABLE 2

|  | Molar ratio | | | | Temperature (°C.) | HCN Feeding Time (hr) | BHC Conversion (%) | NDC's Selectivity (%) |
| --- | --- | --- | --- | --- | --- | --- | --- | --- |
|  | BHC | Ni (O) | ZnCl$_2$ | P (OPh)$_3$ | Liquid HCN | | | |
| Example 7 | 100 | 0.27 | 1.41 | 4.16 | 113 | 95 | 5 | 99.9 | 99.8 |
| Example 8 | 100 | 0.27 | 1.41 | 4.16 | 140 | 65 | 3 | 100 | 99.3 |
| Example 9 | 100 | 0.27 | 1.41 | 4.16 | 95 | 50 | 5 | 94.9 | 98.9 |

TABLE

| | Ni (O) | Neutral ligand | BHC Conversion (%) | NDC's Selectivity (%) |
|---|---|---|---|---|
| Example 10 | Ni[P(O—C₆H₄—CH₃)₃]₄ | P(O—C₆H₄—CH₃)₃ | 100 | 99.5 |
| Example 11 | Ni[P(O—C₆H₄(CH₃))₃]₄ | P(O—C₆H₄(CH₃))₃ | 100 | 99.4 |
| Example 12 | Ni[P(O—C₆H₄—OCH₃)₃]₄ | P(O—C₆H₄—OCH₃)₃ | 100 | 99.6 |
| Example 13 | Ni[P(O—C₆H₄—Cl)₃]₄ | P(O—C₆H₄—Cl)₃ | 100 | 99.5 |

TABLE 4

| | Lewis acid | BHC Conversion (%) | NDC's Selectivity (%) |
|---|---|---|---|
| Example 14 | SnCl₂ | 97.2 | 99.3 |
| Example 15 | CdCl₃ | 98.5 | 99.7 |
| Example 16 | CrCl₃ | 95.6 | 99.5 |
| Example 17 | Al (O-iPr)₃ | 85.9 | 99.0 |
| Example 18 | BPh₃ | 99.9 | 99.8 |

Al (O-iPr)₃: Aluminum isopropoxide
BPh₃: Triphenyl boron

COMPARATIVE EXAMPLE 1

The reaction of Example 1 was repeated with the same feed as in Example 1 except that tetrakis (triphenyl phosphite) nickel was replaced with 0.82 g (0.608 m mol) of tetrakis (triphenyl phosphite) palladium. As a result, the conversion of BHC was 31.6% and the selectivity of NDC's 93.1%.

COMPARATIVE EXAMPLE 2

The reaction of Example 6 was repeated with the same feed as in Example 6 except that zinc chloride was not used.

As a result, the conversion of BHC was 4.1% and the selectivity of NDC's 21.5%.

Industrial Applicability

NDC's produced by the present invention can be hydrogenated to prepare the corresponding diamines, and the diamines may be reacted with aliphatic dicarboxylic acids to produce polyamide resins. Therefore, the NDC's are useful as intermediates for organic syntheses.

We claim:

1. A process for producing a norcamphane dicarbonitrile which comprises hydrocyanating for a feed time of 5 hours or less in a liquid phase bicyclo [2,2,1]-5-heptene-2-carbonitrile of the formula (I):

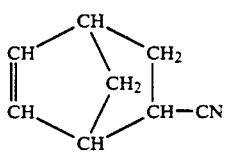

to produce a yield of above 80% of a norcomphane dicarbonitrile of the formula (II):

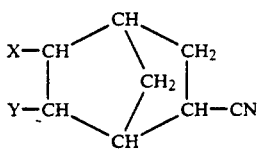

where X and Y are selected from the group consisting of hydrogen and cyano provided that X and Y are different, in the presence of a zero-valent nickel complex catalyst represented by the formula (III):

where A, B, C and D are, similar or dissimilar, neutral ligands of formula (IV):

P (x) (y) (z)    (IV)

where P is a phosphorus atom, x, y and z are similar or dissimilar groups represented by OR where R is selected from the group consisting of alkyl having 18 carbon atoms or less and aryl having 18 carbon atoms or less; neutral ligand of the formula (V):

P (x) (y) (z)    (V)

where P is a phosphorus atom and x, y and z are similar or dissimilar groups represented by OR where R is selected from the group consisting of alkyl having 18 carbon atoms or less and aryl having 18 carbon atoms or less and a Lewis acid.

2. The process according to claim 1, wherein the zero-valent nickel complex catalyst is tetrakis (triaryl phosphite) nickel or tetrakis (trialkyl phosphite) nickel.

3. The process according to claim 2, wherein the zero-valent nickel complex catalyst is tetrakis (triphenyl phosphite) nickel or tetrakis (tri-substituted phenyl phosphite) nickel.

4. The process according to claim 3, wherein the tetrakis (tri-substituted phenyl phosphite) nickel is a member selected from the group consisting of tetrakis (tri-halo-substituted phenyl phosphite) nickel, tetrakis (tri-alkoxy-substituted phenyl phosphite) nickel and tetrakis (tri-alkyl-substituted phenyl phosphite) nickel.

5. The process according to claim 4, wherein the tetrakis (tri-substituted phenyl phosphite) nickel is a member selected from the group consisting of tetrakis (tri-m or p-tolyl phosphite) nickel, tetrakis (tri-m or p-chlorophenyl phosphite) nickel, tetrakis (tri-m or p-methoxyphenyl phosphite) nickel and tetrakis (tri-m or p-nonylphenyl phosphite) nickel.

6. The process according to claim 2, wherein the tetrakis (trialkyl phosphite) nickel is a member selected from the group consisting of tetrakis (triethyl phosphite) nickel, tetrakis (triisopropyl phosphite) nickel and tetrakis (tributyl phosphite) nickel.

7. The process according to claim 1, wherein the Lewis acid is a compound composed of an anion and a metal cation of an element selected from the group consisting of groups IIa, IIIa, IVa, Va, VIa, VIIa, VIII, Ib, IIb, IIIb, and IVb of the Periodic Table.

8. The process according to claim 7, wherein the Lewis acid contains a cation of a metal selected from the group consisting of zinc, cadmium, beryllium, aluminum, gallium, indium, silver, titanium, zirconium, hafnium, germanium, tin, vanadium, niobium, scandium, chromium, molybdenum, tungsten, manganese, rhenium, palladium, thorium, erbium, iron, cobalt, and boron.

9. The process according to claim 7, wherein the anion of the Lewis acid is an anion selected from the group consisting of anions of chlorine, bromine, fluorine and iodine, anions of lower fatty acid of $C_2$–$C_7$, $HPO_3^{2-}$, $H_2PO_2^-$, $CF_3CO_2^-$, $OSO_2C_7F_{15}^-$, and $SO_4^{2-}$.

10. The process according to claim 8, wherein the anion of the Lewis acid is an anion selected from the group consisting of anions of chlorine, bromine, fluorine and iodine, anions of lower fatty acid of $C_2$–$C_7$, $HPO_3^{2-}$, $H_2PO_2^-$, $CF_3CO_2^-$, $OSO_2C_7F_{15}^-$, and $SO_4^{2-}$.

11. The process according to claim 8, wherein the metal cation of the Lewis acid is a metal cation selected from the group consisting of zinc, cadmium, titanium, tin, vanadium, chromium, and aluminum ions.

12. The process according to claim 9, wherein the anion of the Lewis acid is a member selected from the group consisting of chlorine ion, iodine ion, $HPO_3^{2-}$ and $H_2PO_2^-$.

13. The process according to claim 1, wherein the Lewis acid is a member selected from the group consisting of zinc chloride, cadmium chloride, cadmium iodide, chromium chloride, boron trichloride and triphenyl boron.

14. The process according to claim 13, wherein the Lewis acid is zinc chloride.

15. The process according to claim 1, wherein the Lewis acid is organic boron or metal alkoxide.

16. The process according to claim 15, wherein the Lewis acid is a member selected from the group consisting of trialkyl boron, triphenyl boron, aluminum alkoxide and titanium alkoxide.

17. The process according to claim 1, wherein the molar ratio of the zero-valent nickel complex catalyst to bicyclo [2,2,1]-5-heptene-2-carbonitrile ranges from 1:5000 to 1:20.

18. The process according to claim 1, wherein the molar ratio of the zero-valent nickel complex catalyst to bicyclo [2,2,1]-5-heptene-2-carbonitrile ranges from 1:2000 to 1:100.

19. The process according to claim 1, wherein the molar ratio of the Lewis acid to the zero-valent nickel complex catalyst ranges from 0.05:1 to 50:1.

20. The process according to claim 1, wherein the molar ratio of the Lewis acid to the zero-valent nickel complex catalyst ranges from 0.5:1 to 5:1.

21. The process according to claim 1, wherein the total neutral ligand per mole of the zero-valent nickel complex catalyst is 5 moles or more.

22. The process according to claim 1, wherein the total neutral ligand per mole of the zero-valent nickel complex catalyst is from 6 to 36 moles.

23. The process according to claim 1, wherein the total neutral ligand per mole of the zero-valent nickel complex catalyst is from 8 to 20 moles.

24. The process according to claim 1, wherein the reaction temperature of the hydrocyanation is in the range of from −20° to 200° C.

25. The process according to claim 1, wherein the reaction temperature is from 20° to 130° C.

26. The process according to claim 1, wherein the reaction temperature is from 50° to 100° C.

27. The process according to claim 1, wherein hydrogen cyanide is introduced in the form of a gas or liquid.

28. The process according to claim 1, wherein the molar ratio of hydrogen cyanide to BHC is in the range of from 0.2:1 to 1.5:1.

29. The process according to claim 1, wherein the molar ratio of hydrogen cyanide to BHC is in the range of from 0.5:1 to 1.2:1.

30. A process for producing a norcamphane dicarbonitrile which comprises hydrocyanating bicyclo [2,2,1]-5-heptene-2-carbonitrile of the formula (I):

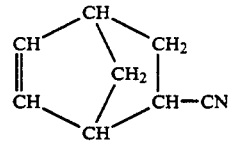

(I)

to produce a norcamphane dicarbonitrile of the formula (II):

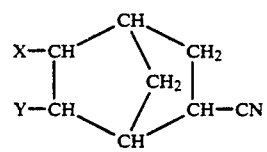

(II)

where X and Y are hydrogen or cyano and X and Y are different from each other, the hydrocyanation being carried out in a liquid phase in the presence of tetrakis (triphenyl or tri-substituted phenyl phosphite) nickel as a zero-valent nickel complex catalyst, triphenyl phosphite of tri-substituted phenyl phosphite as a neutral ligand, and a compound composed of a cation of a metal selected from the group consisting of zinc, cadmium, beryllium, aluminum, gallium, indium, silver, titanium, zirconium, hafnium, germanium, tin, vanadium, niobium, scandium, chromium, molybdenum, tungsten, manganese, rhenium, palladium, thorium, erbium, iron, cobalt, and boron, and an anion selected from the group consisting of halogen, $HPO_3{}^{2-}$, $H_2PO_2{}^-$, $CF_3CO_2{}^-$, $OSO_2C_7F_{15}{}^-$, and $SO_4{}^{2-}$, metal alkoxide, or triaryl boron as a Lewis acid, by introducing from 0.2 to 1.5 moles of hydrogen cyanide per mole of bicyclo [2,2,1]-5-heptene-2-carbonitrile into a catalyst solution where the molar ratio of bicyclo [2,2,1]-5-heptene-2-carbonitrile to the zero-valent nickel complex catalyst ranges from 5000:1 to 20:1, the molar ratio of the Lewis acid to the zero-valent nickel complex catalyst ranges from 0.05:1 to 50:1, and the total neutral ligand per mole of the zero-valent nickel complex catalyst is 5 moles or more, and heating at a temperature of from 20° to 130° C.

31. The process according to claim 30, wherein the molar ratio of the total neutral ligand to the zero-valent nickel complex catalyst ranges from 6:1 to 36:1.

32. The process according to claim 30, wherein the tetrakis (tri-substituted phenyl phosphite) nickel is a member selected from the group consisting of tetrakis (tri-m or p-tolyl phosphite) nickel, tetrakis (tri-m or p-chlorophenyl phosphite) nickel, tetrakis (tri-m or p-methoxyphenyl phosphite) nickel and tetrakis (tri-m or p-nonylphenyl phosphite) nickel.

* * * * *

UNITED STATES PATENT AND TRADEMARK OFFICE
CERTIFICATE OF CORRECTION

PATENT NO.  : 5,169,971
DATED       : December 8, 1992
INVENTOR(S) : Inomata et al.

It is certified that error appears in the above-identified patent and that said Letters Patent is hereby corrected as shown below:

In column 8, line 35, amend "norcomphane" to --norcamphane--; and line 50, amend the formula to read:

-- Ni [ (A) (B) (C) (D) ] --

Signed and Sealed this

Eighth Day of February, 1994

Attest:

BRUCE LEHMAN

Attesting Officer    Commissioner of Patents and Trademarks